US010400073B2

(12) United States Patent
Cammage et al.

(10) Patent No.: US 10,400,073 B2
(45) Date of Patent: Sep. 3, 2019

(54) METHOD FOR THE SURFACE CROSSLINKING OF POLYMER PARTICLES

(71) Applicant: Arkema France, Colombes (FR)

(72) Inventors: Geoffroy Cammage, Rouen (FR); Nicolas Dufaure, Bernay (FR); Guillaume Le, Colombelles (FR); Cyrille Mathieu, Rouen (FR)

(73) Assignee: Arkema France, Colombes (FR)

( * ) Notice: Subject to any disclaimer, the term of this patent is extended or adjusted under 35 U.S.C. 154(b) by 141 days.

(21) Appl. No.: 14/891,514

(22) PCT Filed: May 16, 2014

(86) PCT No.: PCT/EP2014/060105
§ 371 (c)(1),
(2) Date: Apr. 25, 2016

(87) PCT Pub. No.: WO2014/184351
PCT Pub. Date: Nov. 20, 2014

(65) Prior Publication Data
US 2016/0152782 A1 Jun. 2, 2016

(30) Foreign Application Priority Data
May 17, 2013 (FR) ...................... 13 54473

(51) Int. Cl.
C08L 77/00 (2006.01)
C08G 69/00 (2006.01)
C08J 3/24 (2006.01)
A61K 8/88 (2006.01)
C08G 73/14 (2006.01)
A61Q 1/12 (2006.01)
A61Q 19/00 (2006.01)
A61K 8/84 (2006.01)
A61K 8/87 (2006.01)
A61K 8/02 (2006.01)
C08G 69/48 (2006.01)
C08L 77/02 (2006.01)
C08L 77/06 (2006.01)
C08L 79/02 (2006.01)
C08L 79/08 (2006.01)
B29C 64/153 (2017.01)
B29K 77/00 (2006.01)
B29K 79/00 (2006.01)

(52) U.S. Cl.
CPC .............. C08J 3/245 (2013.01); A61K 8/022 (2013.01); A61K 8/84 (2013.01); A61K 8/87 (2013.01); A61K 8/88 (2013.01); A61Q 1/12 (2013.01); A61Q 19/00 (2013.01); B29C 64/153 (2017.08); C08G 69/48 (2013.01); C08G 73/14 (2013.01); C08L 77/02 (2013.01); C08L 77/06 (2013.01); C08L 79/02 (2013.01); C08L 79/08 (2013.01); B29K 2077/00 (2013.01); B29K 2079/085 (2013.01); C08J 2375/04 (2013.01); C08J 2377/02 (2013.01); C08J 2379/02 (2013.01); C08J 2379/08 (2013.01); C08J 2479/08 (2013.01)

(58) Field of Classification Search
CPC ........ C08J 3/245; C08G 69/48; C08G 177/02; C08G 177/06
See application file for complete search history.

(56) References Cited

U.S. PATENT DOCUMENTS

| 4,498,957 | A | * | 2/1985 | Sasaki | D21H 13/26 162/146 |
| 4,694,063 | A | | 9/1987 | Hilaire | |
| 4,702,840 | A | * | 10/1987 | Degen | B01D 67/0011 210/490 |
| 4,737,304 | A | | 4/1988 | VoDinh | |
| 5,597,873 | A | * | 1/1997 | Chambers | C08F 8/14 525/330.1 |
| 6,399,714 | B1 | * | 6/2002 | Huang | C08G 18/603 428/422 |
| 7,211,615 | B2 | | 5/2007 | Baumann | |
| 7,700,124 | B2 | | 4/2010 | Loyen | |
| 2006/0205883 | A1 | * | 9/2006 | Loyen | C08F 283/04 525/242 |
| 2008/0182960 | A1 | | 7/2008 | Ganapathiappan | |
| 2010/0098880 | A1 | | 4/2010 | Senff | |

FOREIGN PATENT DOCUMENTS

| DE | 10251790 | 5/2004 |
| EP | 0192515 | 8/1986 |
| EP | 0471566 | 2/1992 |
| EP | 1661546 | 5/2006 |
| FR | 2588262 | 4/1987 |
| FR | 2910907 | 7/2008 |

OTHER PUBLICATIONS

International Search Report for International Application No. PCT/EP2014/060105 dated Jul. 3, 2014.
Written Opinion of the International Searching Authority for International Application No. PCT/ EP2014/060105 dated Jul. 3, 2014.

* cited by examiner

Primary Examiner — Michael L Leonard
(74) Attorney, Agent, or Firm — RatnerPrestia

(57) ABSTRACT

The invention concerns a method for the surface crosslinking of a polymer, in particle form, having one or a plurality of labile hydrogen functions, comprising a step of implementing a crosslinking agent comprising at least two functions likely to react with the labile hydrogen functions of the polymer, the crosslinking method being carried out at a temperature lower than the melting point of the polymer. The invention also concerns a powder particle and the uses of same.

17 Claims, No Drawings

METHOD FOR THE SURFACE CROSSLINKING OF POLYMER PARTICLES

CROSS-REFERENCE TO RELATED APPLICATIONS

This application is the national phase of International application PCT/EP2014/060105, filed May 16, 2014, which claims priority to French application 1354473, filed May 17, 2013. The disclosures of each of these applications are incorporated herein by reference in their entirety for all purposes.

FIELD OF THE INVENTION

Background of the Related Art

The invention relates to a process for the surface crosslinking of polymer particles. The invention also relates to particles of partially crosslinked polymer obtained by means of said process and to the use of these particles in the field of composites, of structural adhesives, of coatings and of cosmetics. Finally, the present invention relates to a composition comprising said particles.

It has for many years been known practice to incorporate into composite materials polymer powders, generally polyamides, which act as impact reinforcement, placed between the layers of the composite material, or else which act as inert filler. These polymer powders make it possible to improve the mechanical properties of the materials; they can in particular act as a curing agent or anti-delaminating agents.

It is also known practice to use these polymer powders in cosmetic compositions, and in particular in care products, makeup products, fragrancing products or else body hygiene products. These powders confer many properties on the cosmetic compositions containing them, and in particular a soft feel, a powdery finish, a decrease in the greasy sensation sometimes associated with creams, or else a matting effect.

Furthermore, these polymer powders can have a porous structure; they thus allow vectorization of active ingredients and controlled release.

These applications require combinations of specific properties, such as a low moisture uptake, and good ductility, combined with a high melting point. The polymer powders of the prior art exhibit an advantageous compromise between moisture uptake and ductility, but they have the drawback of having a relatively low melting point (Mp), often below 180° C.

Indeed, the use of these powders is limited, when the formulating process requires a high-temperature step.

Coalescence phenomena may be observed, resulting in deformation of the particles, in terms of shape and size, irreversibly damaging the expected mechanical effects.

Thus, there is a real need for polymer particles which have an improved heat resistance, a low moisture uptake, and good chemical resistance, in particular with respect to solvents, and the physicochemical properties of which are preserved during the preparation or the formulation of the material.

SUMMARY OF THE INVENTION

The invention relates to a process for the surface crosslinking of a polymer, in particle form, having one or more labile-hydrogen functions, comprising a step using a crosslinking agent comprising at least two functions capable of reacting with the labile-hydrogen functions of the polymer, the crosslinking process being carried out at a temperature lower than the melting point of the polymer.

The invention also relates to a polymerization process incorporating the abovementioned crosslinking process.

The invention also concerns particles of partially crosslinked polymer powder.

Finally, the present invention relates to a composition comprising said powder.

Finally, the invention concerns the use of these powders in the cosmetics field and in the composite field.

Other characteristics, aspects, subjects and advantages of the present invention will emerge even more clearly on reading the description and the examples which follow.

Furthermore, any range of values denoted by the expression "between a and b" represents the range of values of from more than a to less than b (i.e. limits a and b excluded), while any range of values denoted by the expression "from a to b" signifies the range of values of from a up to b (i.e. including the strict limits a and b).

DETAILED DESCRIPTION OF CERTAIN EMBODIMENTS OF THE INVENTION

For the purposes of the present invention, the terms "particle" and "powder" are used indifferently from one another to denote the form of the polymer. The term "particle" will be used to denote the form of the polymer in an individualized manner, and the term "powder" will be used to denote a set of polymer particles.

The polymer particles according to the invention are in the solid state.

Crosslinking Process

The invention relates to a process for the surface crosslinking of a polymer, in particle form, having one or more labile-hydrogen functions, comprising a step using a crosslinking agent comprising at least two functions capable of reacting with the labile-hydrogen functions of the polymer, the crosslinking process being carried out at a temperature lower than the melting point of the polymer.

Particles

The raw materials for the crosslinking process according to the invention are polymers having one or more labile-hydrogen functions.

The term "labile-hydrogen function" is intended to mean according to the invention a function capable, after the departure of a hydrogen atom, of forming covalent bonds.

Thus, after any possible acid-base reaction caused, for example, by a catalyst, the labile-hydrogen function becomes nucleophilic and reacts with an electrophilic function of the crosslinking agent, to result in the formation of a covalent bond.

By way of example of such functions, mention may be made of hydroxyl (—OH), primary amine (—NH$_2$) or secondary amine (—NHR), primary amide (—CONH—), urea (—NHCONH—) or urethane (—NHCOO—) groups, or else thiol (—SH) groups.

The polymers having one or more labile-hydrogen function(s) according to the invention can preferably be chosen from polymers comprising one or more amide functions, in particular polyamides and polyamide-imides, polyurethanes, polyamines and a blend of these polymers.

Particularly preferably, the polymer having one or more labile-hydrogen function(s) according to the invention is chosen from polyamides and polyamide-imides and a blend thereof; the labile-hydrogen functions are then amide functions. Polyamides are particularly preferred.

The polyamide(s) that is (are) particularly preferred according to the invention can be chosen from polyamides obtained by polycondensation or by anionic polymerization of lactams, of amino acids or of diacids and of diamines.

For the purposes of the present invention, the term "polyamide" is intended to mean a homopolyamide, i.e. a polyamide obtained from a single type of monomer, or a copolyamide, i.e. a polyamide obtained from several types of different monomers.

The repeat unit constituting the polyamide can be chosen from units derived from an amino acid, a lactam and a unit corresponding to the formula (Ca diamine).(Cb diacid), with a representing the number of carbon atoms of the diamine and b representing the number of carbon atoms of the diacid, a and b each ranging from 4 to 36.

When the unit represents a unit derived from an amino acid, it can be chosen from 9-aminononanoic acid (A=9), 10-aminodecanoic acid (A=10), 12-aminododecanoic acid (A=12) and 11-aminoundecanoic acid (A=11) and also its derivatives, in particular N-heptyl-11-aminoundecanoic acid.

When the unit represents a unit derived from a lactam, it can be chosen from pyrrolidinone, 2-piperidinone, caprolactam (A=6), enantholactam, caprylolactam, pelargolactam, decanolactam, undecanolactam and lauryllactam (A=12).

When the unit represents a unit derived from a unit corresponding to the formula (Ca diamine).(Cb diacid), the (Ca diamine) unit is chosen from linear or branched aliphatic diamines, cycloaliphatic diamines and alkylaromatic diamines.

When the diamine is aliphatic and linear, of formula $H_2N-(CH_2)_a-NH_2$, the (Ca diamine) monomer is preferentially chosen from butanediamine (a=4), pentanediamine (a=5), hexanediamine (a=6), heptanediamine (a=7), octanediamine (a=8), nonanediamine (a=9), decanediamine (a=10), undecanediamine (a=11), dodecanediamine (a=12), tridecanediamine (a=13), tetradecanediamine (a=14), hexadecanediamine (a=16), octadecanediamine (a=18), octadecenediamine (a=18), eicosanediamine (a=20), docosanediamine (a=22) and diamines obtained from fatty acids.

When the diamine is aliphatic and branched, it can comprise one or more methyl or ethyl substituents on the main chain. For example, the (Ca diamine) monomer can advantageously be chosen from 2,2,4-trimethyl-1,6-hexanediamine, 2,4,4-trimethyl-1,6-hexanediamine, 1,3-diaminopentane, 2-methyl-1,5-pentanediamine and 2-methyl-1,8-octanediamine.

When the (Ca diamine) monomer is cycloaliphatic, it is preferentially chosen from bis(3,5-dialkyl-4-aminocyclohexyl)methane, bis(3,5-dialkyl-4-aminocyclohexyl)ethane, bis(3,5-dialkyl-4-aminocyclo-hexyl)propane, bis(3,5-dialkyl-4-aminocyclohexyl)butane, bis(3-methyl-4-aminocyclohexyl)methane (BMACM or MACM), p-bis(aminocyclohexyl)methane (PACM) and isopropylidenedi(cyclohexylamine) (PACP). It can also comprise the following carbon-based backbones: norbornylmethane, cyclohexylmethane, dicyclohexylpropane, di(methylcyclohexyl) and di(methylcyclohexyl)propane. A non-exhaustive list of these cycloaliphatic diamines is given in the publication "Cycloaliphatic Amines" (Encyclopedia of Chemical Technology, Kirk-Othmer, 4th Edition (1992), pp. 386-405).

When the (Ca diamine) monomer is alkylaromatic, it is preferentially chosen from 1,3-xylylenediamine and 1,4-xylylenediamine.

When the unit is a unit corresponding to the formula (Ca diamine).(Cb diacid), the (Cb diacid) unit is chosen from linear or branched aliphatic diacids, cycloaliphatic diacids and aromatic diacids.

When the (Cb diacid) monomer is aliphatic and linear, it is chosen from succinic acid (b=4), pentanedioic acid (b=5), adipic acid (b=6), heptanedioic acid (b=7), octanedioic acid (b=8), azelaic acid (b=9), sebacic acid (b=10), undecanedioic acid (b=11), dodecanedioic acid (b=12), brassylic acid (b=13), tetradecanedioic acid (b=14), hexadecanedioic acid (b=16), octadecanedioic acid (b=18), octadecenedioic acid (b=18), eicosanedioic acid (b=20), docosanedioic acid (b=22) and fatty acid dimers containing 36 carbons.

The fatty acid dimers mentioned above are dimerized fatty acids obtained by oligomerization or polymerization of hydrocarbon-based, long-chain unsaturated monobasic fatty acids (such as linoleic acid and oleic acid), as described in particular in document EP 0 471 566.

When the diacid is cycloaliphatic, it can comprise the following carbon-based backbones: norbornylmethane, cyclohexylmethane, dicyclohexylmethane, dicyclohexylpropane, di(methylcyclohexyl) and di(methylcyclohexyl) propane.

When the diacid is aromatic, it is preferentially chosen from terephthalic acid (denoted T), isophthalic acid (denoted I) and naphthalenic diacids.

The polyamides may be crystalline or amorphous and transparent.

Preferably, the polyamides according to the invention are chosen from aliphatic polyamides, more particularly those of which the chain length of the units ranges from 4 to 18, more particularly from 4 to 12. More preferentially, the polyamides according to the invention are chosen from PA6, PA11, PA12, PA6/12, PA6.12, PA6.6, PA8, PA4, PA4.6, PA10.10, PA6.10 and PA10.12, and a blend of these polymers. Preferably, the polyamide is a PA12.

According to another preferred embodiment of the process according to the invention, the polymer having one or more labile-hydrogen function(s) according to the invention is a polyamide-imide, the labile-hydrogen functions then being amide functions.

The polyamide-imide sold under the name Torlon® by the company Solvay is suitable.

Average Diameter

The polymer according to the invention is in the form of a particle, which can be spherical, pseudospherical or angular in shape. Generally, the particle size of the particle depends on the process for producing said particle.

The average diameter of the particle, measured according to standard ISO 13319, can range from 1 to 200 µm, and is particularly between 1 and 200 µm, preferably ranging from 1 to 150 µm, and more particularly is between 1 and 150 µm.

Advantageously, the average diameter of the particle ranges from 1 to 100 µm, preferably from 5 to 100 µm, more particularly from 5 to 60 µm, and even more particularly from 5 to 20 µm.

Preferably, the polymer in particle form that is used belongs to the Orgasol® range sold by Arkema France.

Crosslinking Agent

The crosslinking agent according to the present invention comprises at least two functions capable of reacting with a labile-hydrogen function of the polymer.

In other words, the crosslinking agent comprises at least two electrophilic functions, capable of reacting with a labile-hydrogen function, i.e. a nucleophilic function, of the polymer.

The polyfunctional crosslinking agent according to the invention thus makes it possible to form "bridges" between the various macromolecular chains of the polymer, which are necessarily made by covalent bonds.

The crosslinking agents comprising at least two functions capable of reacting with the functions of the polymer are preferably compounds bearing the following functions: isocyanate, carbodiimide, epoxy, acyllactam, oxazoline and its isomers, oxazine and its isomers, and $PCl_3$.

Preferably, the crosslinking agents have isocyanate functions; they are polyisocyanates.

By way of polyfunctional crosslinking agent that is particularly preferred according to the invention, mention may in particular be made of xylylene diisocyanate, isophorone diisocyanate, naphthalene-1,5-diisocyanate, diphenylmethane-4,4'-diisocyanate, triphenylmethane-4,4',4"-triisocyanate, toluene-2,4-diisocyanate and alkylene diisocyanates, and more preferentially hexamethylene diisocyanate (denoted HMDI).

By way of example, the following reaction scheme (I) illustrates a crosslinking reaction between a polyamide chain and a polyfunctional crosslinking agent, in this case hexamethylene diisocyanate.

A catalysis step resulted in the formation of an amidate, originating from one of the labile-hydrogen functions of the polymer.

The choice of the crosslinking agent can thus influence the physicochemical properties of the desired final material.

The crosslinking agent used in the process according to the invention may be in a content of from 0.1 to 15 mol %, preferably from 0.5 to 10 mol %, relative to the total number of moles of the monomers constituting the polymer having one or more labile-hydrogen function(s) according to the invention.

Addition Step

The step of addition of the crosslinking agent to the powder of polymer having one or more labile-hydrogen function(s) according to the invention can be carried out in the following way:

(1) either by impregnating the crosslinking agent directly onto the particles, if said agent is liquid or in a solvent, and then heating in order to initiate the reaction;

(2) or by placing the polymer powder in a solid/liquid dispersion in a solvent of the crosslinking agent and then adding the crosslinking agent thereto at the reaction temperature in order to initiate the crosslinking reaction.

Those skilled in the art are capable of choosing the appropriate solvent for the crosslinking agent. Mention may in particular be made of paraffinic hydrocarbon fractions for HMDI for example.

Preferably, the process according to the invention neither uses nor results in a latex.

Reaction Scheme (1)

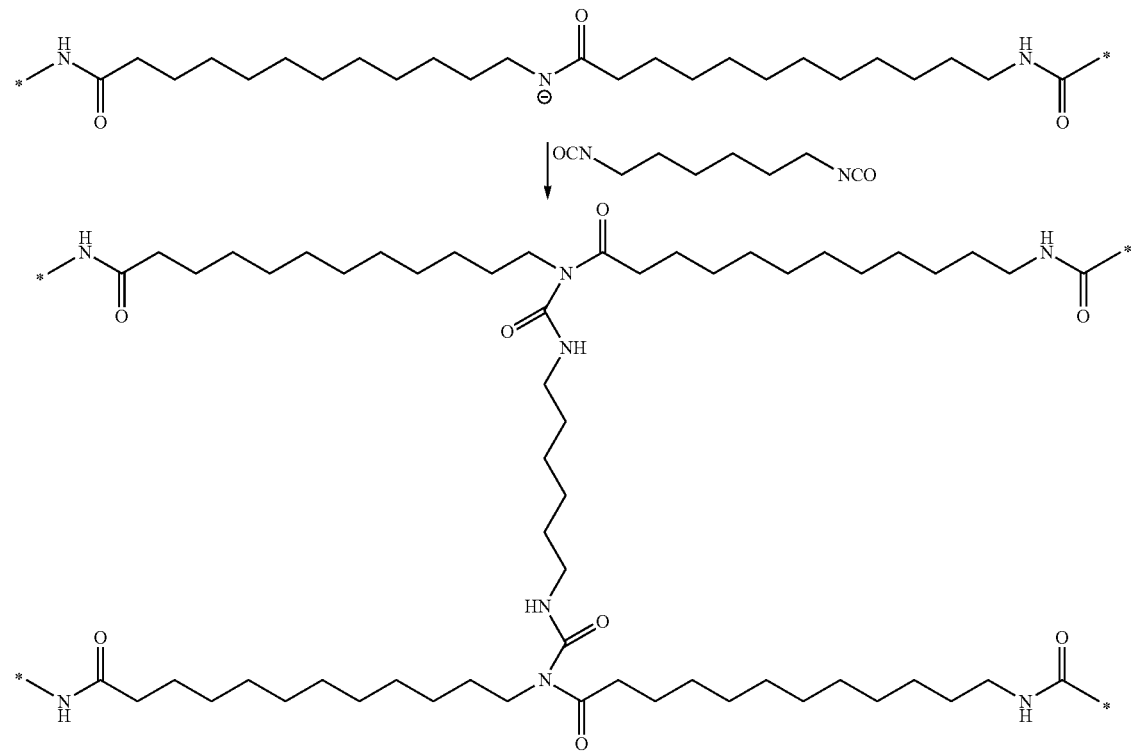

According to one embodiment of the process according to the invention, the polymers having one or more labile-hydrogen function(s) according to the invention may be polymers which are already crosslinked, but which still comprise labile-hydrogen function(s) capable of reacting with a crosslinking agent, identical to or different than the crosslinking agent already used.

The reaction must take place at a temperature lower than the melting of the polymer so that the powder does not agglomerate.

Reactive-Species Formation Step

It may be that a prior step of formation of reactive species of the polymer is required. In order to generate the reactive species, i.e. nucleophilic species, it is possible to use a base that is sufficiently strong to pull the labile hydrogens from the polymer.

These bases can be chosen from sodium hydride, potassium hydride, sodium, sodium methoxide and/or sodium ethoxide.

The amount of base can generally range from 0.1 to 3 mol for 100 mol of polymer, and preferably is between 0.1 and 3 mol for 100 mol of polymer.

This process for the surface crosslinking of a polymer particle results in particles of partially crosslinked polymer. Indeed, the polymer particle will comprise one or more areas of crosslinked polymer, according to the content of crosslinking agent used during the process.

More specifically, the area of crosslinked polymer is a layer which is more or less thick, depending on the content of crosslinking agent introduced and the duration of the crosslinking reaction, lying on the surface of the particle, i.e. on a core of polymer having one or more labile-hydrogen function(s) according to the invention. The layer is then a gradient of composition of crosslinked polymer which is increasingly concentrated in terms of crosslinking nodes with increasing distance from the core.

According to one embodiment of the process according to the invention, the polymer having one or more labile-hydrogen function(s) is polyamide and the crosslinking agent is a polyisocyanate. The process then results in a powder of core-shell structure having a polyamide core and a polyamide-imide shell which is increasingly concentrated in terms of imide functions with increasing distance from the core.

According to another embodiment of the process according to the invention, the polymer having one or more labile-hydrogen function(s) is polyamide-imide and the crosslinking agent is a polyisocyanate. The process then results in a powder of core-shell structure having a polyamide-imide core and a polyamide-imide shell which is increasingly concentrated in terms of imide functions with increasing distance from the core.

The advantage provided by this process is that it makes it possible to control the thickness of the layer of crosslinked polymer and also the nature of the "bridges" between the macromolecular chains by virtue of the nature of the crosslinking agent.

Polymerization Process

The crosslinking process according to the invention can be carried out on polymer powders, as "final" product. It can also be incorporated into a polymerization process.

When the polymer according to the invention is a polyamide, it can, for example, constitute one of the final steps of the polycondensation process or else of an anionic polymerization process.

A subject of the invention is also a process for the polymerization of a polymer in powder form, comprising the following successive steps:
  a polymerization step,
  a step of crosslinking, as defined above, of the polymer in powder form obtained in the previous step, and
  an optional step of neutralization of the reaction medium.

Preferably, the polymerization step is a step of anionic polymerization in solution in a solvent, in the presence of a catalyst and of an activator.

Preferably, the powder is a polyamide powder. More particularly, the process targets the polymerization of amide, such as the polymerization of lactam 6, of lactam 12 or of a mixture thereof. The polymerization is carried out in the presence of a catalyst and of an activator.

As regards the anionic polymerization which is carried out in order to obtain the PA particles, it is carried out in a solvent.

Solvent

The solvent used dissolves the monomer but not the polymer particles which form during the polymerization. Examples of solvent are given in patent EP192515. Advantageously, the solvent is a paraffinic hydrocarbon fraction, the boiling range of which is from 120 to 170° C., and is advantageously between 120 and 170° C., preferably from 140 to 170° C., and advantageously is between 140 and 170° C. The solvent may be supersaturated with monomer at the initiation temperature, i.e. at the temperature at which the polymerization begins.

It is also possible to carry out the polymerization in a solvent that is not supersaturated with monomer. In this case, the reaction medium contains the monomer dissolved in the solvent at a concentration which is far from supersaturation at the initiation temperature.

Catalyst

A catalyst is chosen from the usual catalysts for the anionic polymerization of lactams. It is a base that is sufficiently strong to result, in the case of a lactam, in a lactamate after reaction with the lactam. A combination of several catalysts can be envisioned. By way of nonlimiting examples, mention may be made of sodium hydride, potassium hydride, sodium, sodium methoxide and/or sodium ethoxide. The amount of catalyst(s) introduced can generally range from 0.5 to 3 mol for 100 mol of monomer, and advantageously is between 0.5 and 3 mol for 100 mol of monomer.

Activator

An activator, the role of which is to bring about and/or accelerate the polymerization, is also added. The activator is chosen from lactams-N-carboxyanilides, (mono)isocyanates, polyisocyanates, carbodiimides, cyanamides, acyllactams and acylcarbamates, triazines, ureas, N-substituted imides, phosphorus trichloride and esters. It can optionally also be a mixture of several activators. The activator can also optionally be formed in situ, for example, by reaction of an alkyl isocyanate with the lactam to give an acyllactam. The catalyst/activator mole ratio ranges from 0.2 to 2, advantageously is between 0.2 and 2, preferably from 0.8 to 1.2, and advantageously is between 0.8 and 1.2.

It is possible to add, to the reaction medium, any type of filler (pigments, dyes, carbon black, carbon nanotubes, etc.) or additive (antioxidants, anti-UV agents, plasticizers, etc.), provided that all these compounds are thoroughly dry and inert with respect to the reaction medium.

Polymerization

The anionic polymerization is carried out continuously or else, preferably, batchwise. When carried out batchwise, the solvent is introduced and then, simultaneously or successively, the monomer(s), the catalyst and the activator. It is recommended to introduce first the solvent and the monomer(s), and then to remove any trace of water, for example using azeotropic distillation, then to add the catalyst once the medium is anhydrous. It may be advantageous, in order to prevent solidification from occurring or in order to prevent loss of control of the polymerization, to introduce the activator not all at once but incrementally or else at a given rate of introduction. The polymerization is carried out at atmospheric pressure or else under a slightly greater pressure (partial pressure of the hot solvent) and at a temperature ranging from 20° C. to the boiling point of the solvent.

The initiation temperature and the temperature for polymerization of the lactams generally ranges from 70 to 150° C., is advantageously between 70 and 150° C., preferably from 80 to 130° C., and is advantageously between 80 and 130, and advantageously <120° C. and >90° C.

The crosslinking reaction is then carried out by adding the crosslinking agent as defined above.

Finally, the polymerization ends with a neutralization step.

Powder Particles

The powder particles according to the invention are obtained by means of the crosslinking process described above. The particles according to the invention are also capable of being obtained by means of the crosslinking process described above.

The particle of polymer powder according to the invention comprises
- one or more areas consisting of polymer having one or more labile-hydrogen function(s), as defined above, and
- one or more areas comprising said polymer crosslinked with the crosslinking agent as defined above.

Preferably, the particle of powder comprises
- a core consisting of polymer having one or more labile-hydrogen function(s), as defined above, and
- a layer, placed on said core, comprising said polymer crosslinked with the crosslinking agent as defined above.

The layer of crosslinked polymer is a gradient of composition of crosslinked polymer which is increasingly concentrated in terms of crosslinking nodes with increasing distance from the core.

According to a first embodiment, the layer of crosslinked polymer can be an external layer, intended to be in contact with the air. The particle according to this embodiment then has a core-shell structure.

According to a second embodiment, the layer of crosslinked polymer can constitute an intermediate layer, intended to be inserted into a multilayer structure. The crosslinked layer can be between two layers of optionally crosslinked polymer.

According to a third embodiment, the particle can comprise several layers of polymer crosslinked with different crosslinking agents.

The shape of the particles according to the invention depends on the shape of the particles of the initial polymer having one or more labile-hydrogen function(s).

The thickness of the layer of crosslinked polymer will depend on the amount of the crosslinking agent introduced during the crosslinking process and on the duration of the crosslinking step.

The particle size of the particle according to the invention depends on the particle size of the particle of initial polymer having one or more labile-hydrogen function(s).

The advantage of the crosslinking process according to the invention is that it preserves the particle size dispersion of the powder which is the initial reagent, i.e. the average size and the narrow distribution. Furthermore, on fusion, the particles of powder according to the invention retain the shape of the initial particle.

This property is highly sought after in particular in the composite field. It is necessary to have as many particles as possible around the target, and very few, or even no, very large particles, so that they can perform their role as a spacer between the sheets of carbon fibers in the composites. Furthermore, the surface porosity of the initial powder remains unchanged. When the initial polymer is crystalline, it has been observed that the crystallinity is also preserved.

The polymer having one or more labile-hydrogen function(s) and the crosslinking agent are as described above for the crosslinking process.

According to one particular embodiment of the invention, the polymer having one or more labile-hydrogen function(s) is polyamide and the crosslinking agent is a polyisocyanate; the particle of core-shell structure will have a polyamide core and a polyamide-imide shell which is increasingly concentrated in terms of imide functions with increasing distance from the core.

According to one preferred embodiment, the polymer having one or more labile-hydrogen function(s) belongs to the Orgasol® product range and the crosslinking agent is a polyisocyanate.

Formulation

The invention also relates to a composition comprising the powder as defined above. Preferably, the composition is a thermosetting composition.

The powder obtained can be used as it is and is introduced into a composition of the anhydrous type or in the form of an oil-in-water (O/W) or water-in-oil (W/O) emulsion.

Preferably, the composition according to the invention comprises a powder as defined above.

When the composition is used in the cosmetics field, it comprises a cosmetically acceptable medium, which may be water, or one or more alcohols and a mixture thereof.

Use

The invention relates to the use of the powder as defined above, in particular as a filler or reinforcement, in composites, in structural adhesives, in substrate coatings, in particular based on powder paint or liquid paint, which can be applied to metal, plastic, wood, glass, paper or rubber substrates, and in transfer papers.

The invention also relates to the use of the powder as defined above for producing objects by agglomeration of powders by fusion brought about by radiation chosen from a laser beam, infrared radiation or UV radiation.

Finally, the invention relates to the use of the powder as defined above, as an additive in cosmetic compositions.

The following examples serve to illustrate the invention without, however, being limiting in nature.

EXAMPLES

The physicochemical characteristics of the powders exemplified were evaluated according to the following methods:

Measurement of the Average Diameter:

The average diameter of the particles of the powders exemplified is measured according to standard ISO 13319.

Measurement of the Thermal Characteristics:

The analysis of the powders is carried out according to standard ISO 11357-3 "Plastics: Differential scanning calorimetry (DSC) Part 3: Determination of temperature and enthalpy of melting and crystallization."

Measurement of the Enthalpy of Melting:

The enthalpy of melting is directly proportional to the degree of crystallinity of the polymer. A comparison of the enthalpy of melting between two products therefore makes it possible to compare their degree of crystallinity.

The enthalpy of melting is measured by DSC according to standard ISO 11357-3.

Solubility Test:

The solubility is measured by introducing 1 g of powder per liter of hexafluoroisopropanol. These mixtures are maintained at ambient temperature for 24 hours in order to dissolve the non-crosslinked polymer chains.

These solutions are then filtered in order to remove the insoluble part, and then analyzed by SEC using a Waters Alliance 2695 apparatus. A Waters 2414 RID detector is used. The refractometric response coefficient K(RI) is then measured.

1. Synthesis of a Crosslinked Polyamide 12 Powder 2800 ml of solvent and then successively 899 g of lactam 12, 14.4 g of EBS (ethylenebisstearamide) and 73.0 g of Orgasol® 2002 UD NAT 1 (PA12 powder) are placed in the reactor maintained under nitrogen. After having started the stirring at 300 rpm, heating is carried out gradually up to 110° C., and then 280 ml of solvent are distilled off under vacuum in order to azeotropically entrain any trace of water that might be present.

After a return to atmospheric pressure, the anionic catalyst: 2.2 g of sodium hydride at 60% purity in oil, is then rapidly introduced under nitrogen and stirring is increased to 700 rpm, under nitrogen at 105° C.

This temperature is then maintained for 30 minutes. By virtue of a metering pump, the chosen activator, namely stearyl isocyanate (38.3 g made up to 153.0 g with solvent), is continuously injected into the reaction medium according to the following program: 51 g/h for three hours and then the temperature is raised to 120° C. for two hours.

The step of surface crosslinking the powder obtained is carried out as follows. At 120° C. with stirring, a solution of hexamethylene diisocyanate: 5 mol % of HMDI relative to the lactam 12, is added to the reaction medium for three hours, and the mixture is then left for a further two hours in order to finish all the reactions.

The powder is then filtered and dried in order to be neutralized with an aqueous $H_3PO_4$ solution. The neutralized powder is then again dried. In order to verify the efficiency of the crosslinking, the powder is immersed in m-cresol at 90° C.; insoluble particles appear, characterizing good crosslinking of the polyamide (no insoluble material in the case of Orgasol 2002 D Nat1).

Evaluation of the Powder:

Two types of powder were compared:
a commercial powder called Orgasol® 2002 D NAT 1, which is not crosslinked; this powder constitutes the comparative powder A. It corresponds to a powder prepared according to the process previously described, but without the crosslinking step,
the powder according to the invention denoted B, which is obtained using the process according to example 1.

Solubility Test:

The refractometric response coefficient K(RI) is measured. The K(RI) is directly proportional to the concentration of PA12 in HFIP. A coefficient of 201 is measured for the Orgasol® 2002 D Nat 1, and a coefficient of 45 is measured for the powder of the invention.

The results are given in table 1 below.

TABLE 1

|  | Comparative powder (L12) A | Powder according to the invention (L12) B |
|---|---|---|
| Average diameter (μm) | 19.0 | 19.0 |
| Melting point (° C.) | 180 | 183 |
| Enthalpy of fusion (J/g) | 113 | 108 |
| Solubility in HFIP (%) | 100 | 23 |

These results demonstrate the fact that the particle size of the initial powder is preserved.

The test on the enthalpy of melting shows that the crosslinking of the powder does not in any way modify the crystallinity of the material.

The results relating to the solubility of the powders show that the crosslinking of the powder has indeed taken place. Furthermore, this test demonstrates the solvent-resistance of the powder B according to the invention.

2. Synthesis of a Crosslinked PA6 Powder 2452 ml of solvent and then successively 919.3 g of lactam 6 (caprolactam), 4.7 g of EBS (ethylenebisstearamide) and 10.5 g of Aerosyl® R972 are placed in the reactor maintained under nitrogen. After having started the stirring at 300 rpm, heating is carried out gradually up to 110° C., and then 294 ml of solvent are distilled off under vacuum in order to azeotropically entrain any trace of water that might be present.

After a return to atmospheric pressure, the anionic catalyst: 6.3 g of sodium hydride at 60% purity in oil, is then rapidly introduced under nitrogen and the stirring is increased to 900 rpm, under nitrogen at 105° C. This temperature is then maintained for 30 minutes. By virtue of a metering pump, the chosen activator, namely stearyl isocyanate (27.3 g made up to 147.1 g with solvent), is continuously injected into the reaction medium according to the following program: 49 g/h for three hours and then the reaction takes place for a further two hours at 120° C.

The step of surface crosslinking the powder obtained is carried out as follows. At 120° C. with stirring, a solution of hexamethylene diisocyanate: 5 mol % of HMDI relative to the lactam 6, is added to the reaction medium for three hours, and then the resulting mixture is left for a further two hours in order to consume all the reactive functions.

The powder is then filtered and dried in order to be neutralized with an aqueous $H_3PO_4$ solution. The neutralized powder is then again dried.

Evaluation of the Powder:

Two types of powder were compared:
a commercial powder called Orgasol® 1002 D Nat1, which is not crosslinked; this powder constitutes the comparative powder C. It corresponds to a powder prepared according to the process previously described, but without the crosslinking step,
the powder according to the invention denoted D, which is obtained using the process according to example 2.

Solubility Test

The powders are immersed in m-cresol at 90° C. Insoluble particles appear, characterizing good crosslinking of the polyamide D. There is no appearance of insoluble material in the case of the comparative powder C.

The refractometric response coefficient K(RI) is measured. The K(RI) is directly proportional to the concentration of PA6 in HFIP. A coefficient of 209 is measured for the comparative powder C, and a coefficient of 82 is measured for the powder D according to the invention.

The results are given in table 2 below.

TABLE 2

|  | Comparative powder (PA6) C | Powder according to the invention (PA6) D |
|---|---|---|
| Average diameter (μm) | 20.9 | 20.9 |
| Melting point (° C.) | 210 | 205 |
| Enthalpy of melting (J/g) | 116 | 109 |
| Solubility in HFIP (%) | 100 | 38 |

3. Synthesis of a Crosslinked Polyamide-Imide Powder
Synthesis of the Polyamide:

2800 ml of solvent and then successively 919.3 g of lactam 12 (lauryllactam), 14.7 g of EBS (ethylenebisstearamide) and 1.84 g of Sipernat® 320DS are placed in the reactor maintained under nitrogen. After having started the stirring at 300 rpm, heating is carried out gradually up to 110° C., and then 280 ml of solvent are distilled off under vacuum in order to azeotropically entrain any trace of water that might be present.

After a return to atmospheric pressure, the anionic catalyst: 2.36 g of sodium hydride at 60% purity in oil, is then rapidly introduced under nitrogen and the stirring is increased to 800 rpm, under nitrogen at 105° C. This temperature is then maintained for 30 minutes. By virtue of a metering pump, the chosen activator, namely stearyl isocyanate (27.3 g made up to 147.1 g with solvent), are continuously injected into the reaction medium according to the following program: 49 g/h for three hours and then the temperature is raised to 120° C. for two hours.

Synthesis of the Polyamide-Imide:

A polyamide-imide powder is obtained as follows. At 120° C. with stirring, a solution of methylenebis(cyclohexyl isocyanate): 0.1 mol % of H12MDI relative to the lactam 12, is added to the reaction medium for three hours, and then the resulting mixture is left for a further two hours in order to consume all the functions of the crosslinking agent. A polyamide-imide powder completely soluble in m-cresol at 90° C., which constitutes the comparative powder E, is then obtained.

Crosslinking of the Polyamide-Imide:

The step of surface crosslinking the powder obtained is carried out as follows. At 120° C. with stirring, a solution of hexamethylene diisocyanate: 4.9 mol % of HMDI relative to the lactam 12, is added to the reaction medium for three hours, and the resulting mixture is then left for a further two hours in order to consume all the reactive functions.

The powder is then filtered and dried in order to be neutralized with an aqueous $H_3PO_4$ solution. The neutralized powder is then again dried.

Evaluation of the Powder:

Two types of powder were compared:
a comparative powder E, resulting from the synthesis of the polyamide-imide, described above;
the powder according to the invention denoted F, which is obtained using the process according to example 3.

Solubility Test

The powders are immersed in m-cresol at 90° C. Insoluble particles appear, characterizing good crosslinking of the polyamide-imide F.

The results are given in table 3 below.

TABLE 3

|  | Comparative powder (PAI) E | Powder according to the invention (PAI) F |
|---|---|---|
| Average diameter (μm) | 49.4 | 49.4 |
| Melting point (° C.) | 178 | 177 |
| Enthalpy of melting (J/g) | 110 | 106 |
| Solubility in HFIP (%) | 100 | 30 |

These examples show that, whatever the type of polymer used, the particle size of the initial powder and the crystallinity of the material are preserved.

The invention claimed is:

1. A process for the surface crosslinking of a polymer, in particle form, comprising at least one amide function, comprising a step of using a crosslinking agent comprising at least two functional groups which each react with a labile hydrogen function of the amide functions of the polymer thereby effecting the crosslinking process, the crosslinking process being carried out at a temperature lower than the melting point of the polymer,
wherein the polymer particles have an average diameter which ranges from 1 to 200 μm, and
wherein the crosslinking agent is selected from the group consisting of a) compounds bearing at least two of the following functional groups: isocyanate, carbodiimide, epoxy, acyllactam, oxazoline and its isomers, oxazine and its isomers, and b) $PCl_3$, and the crosslinking agent is in a content of from 0.1 to 15 mol %, relative to the total number of moles of the monomers constituting the polymer having at least one amide function.

2. The process as claimed in claim 1, wherein the polymer is selected from the group consisting of polyamides and polyamide-imides and blends thereof.

3. The process as claimed in claim 2, wherein the polymer is a polyamide.

4. The process as claimed in claim 3, wherein the polymer is selected from the group consisting of PA6, PA11, PA12, PA6/12, PA6.12, PA6.10, PA10.10, PA10.12, PA6.6, PA8, PA4 and PA4.6, and blends of these polymers.

5. The process as claimed in claim 4, wherein the polymer is PA12.

6. The process as claimed in claim 1, wherein the crosslinking agent is a polyisocyanate.

7. A process for the polymerization of a polymer, comprising the following successive steps:
a polymerization step,
a step of crosslinking, in accordance with the process as claimed in claim 1, of the polymer in powder form obtained in the previous step, and
an optional step of neutralization of the reaction medium.

8. The process as claimed in claim 7, wherein the polymerization step is a step of anionic polymerization in solution in a solvent, in the presence of a catalyst and of an activator.

9. A particle of polymer powder comprising:
one or more areas consisting of polymer having one or more amide function(s), and
one or more area(s) comprising said polymer crosslinked with a crosslinking agent in accordance with the process as claimed in claim 1.

10. The particle as claimed in claim 9, wherein the particle comprises:
a core consisting of polymer having one or more amide function(s), and
a layer comprising said polymer crosslinked with a crosslinking agent in accordance with the process as claimed in claim 1.

11. A composition comprising the particle of powder as claimed in claim 9.

12. A method for producing objects by agglomeration of a powder by fusion brought about by radiation chosen from a laser beam, infrared radiation or UV radiation, wherein the powder is comprised of particles of powder as claimed in claim 9.

13. A method of making cosmetic compositions, comprising using a particle of powder as claimed in claim 9 as an additive.

14. The process as claimed in claim 1, wherein the polymer is a polyamide or blend of polyamides.

15. The process as claimed in claim 1, wherein the crosslinking agent is in a content of from 0.5 to 10 mol %, relative to the total number of moles of the monomers constituting the polymer having one or more amide function(s).

16. The process as claimed in claim 1, wherein the polymer is a polyamide and the crosslinking agent is a polyisocyanate.

17. A method of making an article selected from the group consisting of composites, structural adhesives, substrate coatings and transfer papers, comprising using particles of polymer powder as claimed in claim 9 in the article.

* * * * *